US009946846B2

(12) United States Patent
Morsch et al.

(10) Patent No.: US 9,946,846 B2
(45) Date of Patent: Apr. 17, 2018

(54) VISUALIZING THE DOCUMENTATION AND CODING OF SURGICAL PROCEDURES

(75) Inventors: Mark L. Morsch, San Diego, CA (US); Michael A. Landis, San Diego, CA (US); Blair C. Jennings, San Diego, CA (US)

(73) Assignee: A-LIFE MEDICAL, LLC, San Diego, CA (US)

( * ) Notice: Subject to any disclaimer, the term of this patent is extended or adjusted under 35 U.S.C. 154(b) by 1140 days.

(21) Appl. No.: 12/185,754

(22) Filed: Aug. 4, 2008

(65) Prior Publication Data

US 2009/0070140 A1     Mar. 12, 2009

Related U.S. Application Data

(60) Provisional application No. 60/953,936, filed on Aug. 3, 2007.

(51) Int. Cl.
| | |
|---|---|
| *G06Q 50/00* | (2012.01) |
| *G06F 19/00* | (2018.01) |
| *G06Q 50/22* | (2018.01) |
| *G06Q 10/00* | (2012.01) |

(52) U.S. Cl.
CPC ........ *G06F 19/3487* (2013.01); *G06F 19/363* (2013.01); *G06Q 50/22* (2013.01)

(58) Field of Classification Search
CPC ........ G06Q 50/22; G06Q 50/24; G06Q 40/08; G06Q 10/10; G06F 19/322
USPC ......................................................... 705/2
See application file for complete search history.

(56) References Cited

U.S. PATENT DOCUMENTS

| | | | |
|---|---|---|---|
| 3,996,672 A | 12/1976 | Osofsky et al. | |
| 5,307,262 A | 4/1994 | Ertel | |
| 5,325,293 A * | 6/1994 | Dorne | 705/2 |
| 5,483,443 A | 1/1996 | Milstein et al. | |
| 5,583,758 A * | 12/1996 | McIlroy et al. | 705/2 |
| 5,594,638 A | 1/1997 | Iliff | |
| 5,619,709 A | 4/1997 | Caid et al. | |
| 5,675,819 A | 10/1997 | Schuetze | |
| 5,680,511 A | 10/1997 | Baker et al. | |
| 5,778,157 A | 7/1998 | Oatman et al. | |
| 5,794,178 A | 8/1998 | Caid et al. | |
| 5,809,476 A | 9/1998 | Ryan | |
| 5,873,056 A | 2/1999 | Liddy et al. | |
| 5,900,871 A | 5/1999 | Atkin et al. | |
| 5,963,894 A | 10/1999 | Richardson et al. | |
| 5,995,955 A | 11/1999 | Oatman et al. | |
| 6,055,494 A | 4/2000 | Friedman | |

(Continued)

OTHER PUBLICATIONS

Friedman, et al. "Natural language processing in an operational clinical information system," Natural Language Engineering, vol. 1(1): 83-108 (May 1995).

(Continued)

*Primary Examiner* — Tran N Nguyen
(74) *Attorney, Agent, or Firm* — Dorsey & Whitney LLP (57) ABSTRACT

Among other things, methods, systems and computer program products for providing visual indication of documentation and coding of medical procedures may include providing a choice of medical codes associated with a medical procedure. A user selection of one of the medical codes is detected. Based on the detection, a visual indication of the user selection is generated on one or more anatomical diagrams.

10 Claims, 9 Drawing Sheets

(56) References Cited

U.S. PATENT DOCUMENTS

| | | |
|---|---|---|
| 6,081,774 A | 6/2000 | De Hita et al. |
| 6,137,911 A | 10/2000 | Zhilyaev |
| 6,182,029 B1 | 1/2001 | Friedman |
| 6,389,405 B1 | 5/2002 | Oatman et al. |
| 6,498,982 B2 | 12/2002 | Bellesfield et al. |
| 6,529,876 B1 | 3/2003 | Dart et al. |
| H2098 H | 3/2004 | Morin |
| 6,708,186 B1 | 3/2004 | Claborn et al. |
| 6,866,510 B2 | 3/2005 | Polanyi et al. |
| 6,915,254 B1 | 7/2005 | Heinze et al. |
| 7,043,426 B2 | 5/2006 | Roberge et al. |
| 7,113,905 B2 | 9/2006 | Parkinson et al. |
| 7,174,507 B2 | 2/2007 | Baudin et al. |
| 7,359,861 B2 | 4/2008 | Lee |
| 7,360,151 B1 | 4/2008 | Froloff |
| 7,369,998 B2 | 5/2008 | Sarich et al. |
| 7,493,326 B2 | 2/2009 | Bishop et al. |
| 7,516,125 B2 | 4/2009 | Rao |
| 7,610,190 B2 | 10/2009 | Polanyi et al. |
| 7,624,027 B1 * | 11/2009 | Stern et al. ................... 705/2 |
| 7,653,641 B2 | 1/2010 | Theissen et al. |
| 7,720,723 B2 | 5/2010 | Dicker |
| 7,827,165 B2 | 11/2010 | Abernethy et al. |
| 7,865,358 B2 | 1/2011 | Green et al. |
| 7,908,552 B2 | 3/2011 | Heinze |
| 7,949,538 B2 | 5/2011 | Heinze |
| 8,078,454 B2 | 12/2011 | Pouzin |
| 8,140,323 B2 | 3/2012 | Johnson et al. |
| 8,719,703 B2 | 5/2014 | Bier |
| 9,110,756 B1 | 8/2015 | Guo et al. |
| 9,804,772 B2 | 10/2017 | Oh et al. |
| 2002/0010714 A1 | 1/2002 | Hetherington |
| 2002/0035581 A1 | 3/2002 | Reynar et al. |
| 2002/0085040 A1 | 7/2002 | Krolczyk |
| 2002/0128819 A1 | 9/2002 | Jessee |
| 2002/0156810 A1 | 10/2002 | Holland et al. |
| 2003/0018251 A1 * | 1/2003 | Solomon ................... 600/427 |
| 2003/0033347 A1 | 2/2003 | Bolle et al. |
| 2003/0115039 A1 | 6/2003 | Wang |
| 2003/0115195 A1 | 6/2003 | Fogel et al. |
| 2003/0217052 A1 | 11/2003 | Rubenczyk et al. |
| 2004/0059577 A1 | 3/2004 | Pickering |
| 2004/0064808 A1 | 4/2004 | Kira |
| 2004/0093293 A1 | 5/2004 | Cheung |
| 2004/0117734 A1 | 6/2004 | Krickhahn |
| 2004/0172297 A1 | 9/2004 | Rao et al. |
| 2004/0249638 A1 | 12/2004 | Wang |
| 2004/0254816 A1 * | 12/2004 | Myers ................... 705/2 |
| 2005/0010421 A1 | 1/2005 | Watanabe et al. |
| 2005/0071185 A1 | 3/2005 | Thompson |
| 2005/0091067 A1 | 4/2005 | Johnson |
| 2005/0261910 A1 | 11/2005 | Precoda et al. |
| 2005/0273361 A1 | 12/2005 | Busch |
| 2006/0059021 A1 | 3/2006 | Yulman et al. |
| 2006/0129922 A1 | 6/2006 | Walker |
| 2006/0134750 A1 | 6/2006 | Liu et al. |
| 2006/0149565 A1 | 7/2006 | Riley |
| 2006/0247949 A1 | 11/2006 | Shorrosh |
| 2007/0061348 A1 | 3/2007 | Holland et al. |
| 2007/0094030 A1 | 4/2007 | Xu |
| 2007/0226211 A1 | 9/2007 | Heinze et al. |
| 2007/0237377 A1 | 10/2007 | Oosawa |
| 2007/0294200 A1 | 12/2007 | Au |
| 2008/0222518 A1 | 9/2008 | Walker |
| 2008/0256108 A1 | 10/2008 | Heinze et al. |
| 2008/0256329 A1 | 10/2008 | Heinze et al. |
| 2008/0282153 A1 | 11/2008 | Kindeberg et al. |
| 2009/0070140 A1 | 3/2009 | Morsch et al. |
| 2009/0144617 A1 | 6/2009 | Funes et al. |
| 2009/0175550 A1 | 7/2009 | Taleb |
| 2010/0064131 A1 | 3/2010 | Spatscheck et al. |
| 2010/0082673 A1 | 4/2010 | Nakano |
| 2010/0195909 A1 | 8/2010 | Wasson et al. |
| 2010/0257444 A1 | 10/2010 | Bever et al. |
| 2012/0011470 A1 | 1/2012 | Oh et al. |
| 2012/0136863 A1 | 5/2012 | Bobick et al. |
| 2013/0246480 A1 | 9/2013 | Lemcke et al. |
| 2013/0262125 A1 | 10/2013 | Tunstall-Pedoe |
| 2014/0164388 A1 | 6/2014 | Zhang et al. |

OTHER PUBLICATIONS

Zingmond and Lenert. "Monitoring Free-Text Data Using Medical Language Processing," Computers and Biomedical Research, vol. 26: 467-481 (1993).

Lehnert, Soderland, Aronow, Feng, and Shmueli. "Inductive Text Classification for Medical Applications," to appear in Journal for Experimental and Theoretical Artificial Intelligence, Brookline, MA (date unknown).

Larkey and Croft. "Automatic Assignment of ICD9 Codes to Discharge Summaries," UMass Center for Intelligent Information Retrieval, Amherst, MA (date unknown).

Sneiderman, Rindflesch, and Aronson. "Finding the Findings: Identification of Findings in Medical Literature Using Restricted Natural Language Processing," Bethesda, MD (1996).

Aronow, Cooley, and Soderland. "Automated Identification of Episodes of Asthma Exacerbation for Quality Measurement in a Computer-Based Medical Record," Brookline, MA and Amherst, MA (date unknown).

Croft, Callan, and Aronow. "Effective Access to Distributed Heterogeneous Medical Text Databases," MEDINFO 96 Proceedings, Amherst, MA (1995).

Aronow, Soderland, Feng, Croft and Lehnert. "Automated Classification of Encounter Notes in a Computer Based Medical Record," Amherst, MA (date unknown).

Aronow and Shmueli. "A PC Classifier of Clinical Text Documents: Advanced Information Retrieval Technology Transfer," Amherst, MA (1996).

Aronow and Feng, "Ad-Hoc Classification of Electronic Clinical Documents," D-Lib Magazine, Amherst, MA, 1997.

Soderland, Aronow, Fisher, Aseltine and Lehnert. "Machine Learning of Text Analysis Rules for Clinical Records," Amherst, MA and Brookline, MA (date unknown).

Yang and Chute. "An Application of Least Squares Fit Mapping to Clinical Classification," 16.sup.th Annual Symposium on Computer Application in Medical Care, pp. 460-464, Rochester, MN (1993).

Ranum. "Knowledge Base Understanding of Radiology Text," 12.sup.th Annual Symposium on Computer Application in Medical Care, pp. 141-145, Rochester, MN (1988).

Sager, Lyman, Nhan, and Trick. "Automatic Encoding into SNOMED III: A Preliminary Investigation," 18.sup.th Annual Symposium on Computer Application in Medical Care, pp. 230-234, New York, NY (1994).

Lenert and Tovar. "Automated Linkage of Free-Text Descriptions of Patients with a Practice Guideline," 17.sup.th Annual Symposium on Computer Application in Medical Care, pp. 274-278, Stanford, CA (1993).

Sager, Lyman, Bucknail, Nhan, and Trick. "Natural Language Processing and the Representation of Clinical Data," Journal of the American Medical Information Association, vol. 1, No. 2, pp. 142-160, New York, NY (Mar./Apr. 1994).

Furuse et al. "Constituent Boundary Parsing for Example-Based Machine Translation," Google, pp. 105-111 (1994).

Starosta et al. "Lexicase Parsing: A Lexicon-driven Approach to Syntactic Analysis," Google, pp. 127-132 (1986).

Neubauer, Aljoscha Steffen. "The EWMA control chart," Clinical Chemistry, 43(4): 594-601 (1997).

Department of Health and Human Services—OIG Office of Audit Services. Rat-Stats Companion Manual (Sep. 2001).

Department of Health and Human Services—OIG Office of Audit Services. Rat-Stats User Guide (Sep. 2001).

"Introducing SNOMED CT" (online) [Retrieved Dec. 21, 2010]; Retrieved from the Internet URL: www.ihtsdo.org/publications/introducing-snomed-ct/; 2 pgs.

"Value Proposition for SNOMED CT" (online) [Retrieved Dec. 21, 2010]; Retrieved from the Internet URL: www.ihtsdo.org/fileadmin/

(56) References Cited

OTHER PUBLICATIONS user_upload/Docs_01/Publications/SNOMED_CT/SNOMED_CT_Benefits_v4.pdf; 3 pgs.

"SNOMED Clinical Terms User Guide Jan. 2010 International Release (US English)" (online) [Retrieved Dec. 21, 2010]; Retrieved from the Internet URL: www.ihtsdo.org/fileadmin/user_upload/Docs_01/Publications/doc_userguide_current-en-US_INT_20100131.pdf.; 99 pages.

"SNOMED Clinical Terms Overview" (online) [Retrieved Dec. 21, 2010]; retrieved from the Internet URL: www.ihtsdo.org/fileadmin/user_upload/Docs_01/Recourses/Introducing_SNOMED_CT/SNOMED_CT_Overview)_IHTSDO_Taping_Aug08.pdf.; 82 pgs.

"SNOMED Clinical Terms Basics" (online) [Retrieved Dec. 21, 2010]; retrieved from the Internet URL: www.ihtsdo.org/fileadmin/user_upload/Docs_01/Recourses/Introducing_SNOMED_CT/SNOMED_CT_Basics_IHTSDO_Taping_Aug08.pdf.; 82 pgs.

"SNOMED Clinical Terms Fundamentals" (online) [Retrieved Dec. 21, 2010]; retrieved from the Internet URL: www.ihtsdo.org/fileadmin/user_upload/docs_01/SNOMED_Clinical_Terms_Fundamentals.pdf.; 56 pgs.

"SNOMED CT Browsers" (online) [Retrieved Dec. 21, 2010]; Retrieved from the Internet URL: www.nim.nih.gov/research/umls/Snomed/snomed_browsers.html; 2 pgs.

"HL7 Clinical Document Architecture, Release 2.0" (online) [Retrieved Dec. 20, 2010]; Retrieved from the Internet URL: www.hl7.org/v3ballot/html/foundationdocuments/cda/cda.htm; 190 pgs.

Gregory, Tom, "Interpreting Error Rates in Health Care Billing Audits," Journal of Health Care Compliance; Jan./Feb. 2003; 5, 1; p. 4.

Richardson, S. et al., "MindNet: acquiring and structuring semantic information from text", ACM 1998, pp. 1098-1102. (5 pages).

Zhou, X. et al., "Converting Semi-structured Clinical Medical Records into Information and Knowledge", IEEE 2005, pp. 1-8. (8 pages).

Shaikh, et al., "Assessing Sentiment of Text by Semantic Dependency and Contextual Valence Analysis", Springer 2007, pp. 191-202. (12 pages).

Wattenberg et al., The Word Tree, an Interactive Visual Concordance, IEEE 2008, pp. 1221-1228.

Stoica et al., Nearly-Automated Metadata Hierarchy Creation, ACM 2004, pp. 1-4.

\* cited by examiner

VISUALIZING THE DOCUMENTATION AND CODING OF SURGICAL PROCEDURES

CLAIM OF PRIORITY

This application claims priority under 35 USC § 119(e) to U.S. Patent Application Ser. No. 60/953,936, filed on Aug. 3, 2007, the entire contents of which are hereby incorporated by reference.

TECHNICAL FIELD

The following disclosure relates to medical coding.

BACKGROUND

Medical codes can be assigned from standardized code sets representing the clinically relevant aspects of physician documentation or a patient medical record. The coding of certain medical procedures, such as interventional surgical procedures can be complex due to the difficulty in accurately capturing and codifying the multiple aspects of a procedure.

SUMMARY

Among other things, techniques, methods and computer program products are described for visualizing the documentation and coding of medical procedures.

In one aspect, a choice of medical codes associated with a medical procedure is provided. Also, a user selection of one of the medical codes is detected. Based on the detection, a visual indication of the user selection is generated on one or more anatomical diagrams.

In another aspect, one or more anatomical diagrams associated with a medical procedure are provided. At least one anatomical diagram includes one or more user selectable areas. In addition, a user selection of the one or more user selectable areas on the one or more anatomical diagrams is detected. Based on the detection, a textual description of the user selection is generated.

Implementations can optionally include one or more of the following features. Providing can include presenting the one or more user selectable areas to include one or more catheter insertion locations. In addition, a user selection of one of the one or more catheter insertion locations and a user identification of at least one destination location can be received. The selected catheter insertion location and the identified destination location represent two points on a catheter route. Also, a user selection of another destination location can be received. Medical codes can be obtained based on the user selections of the insertion point and at least one of the two destinations. Obtaining the medical codes can include translating a description of the catheter route into standard medical codes and a series of line segments on the one or more anatomical diagrams. The description of the catheter route can include an ordered sequence of anatomy identifiers that represent parts of an anatomy. Further, the series of line segments can be used to generate a visual indication of the catheter route.

In another aspect, a system of visualizing processes of documentation and coding of medical procedures includes a user input device. The system also includes one or more computer systems coupled to the user input device. The computer systems include a processor and a display that provide a graphical user interface. The graphical user interface includes a text display region to display textual descriptions associated with a medical procedure. The graphical user interface also includes a medical code display region to display user selectable medical codes corresponding to the displayed textual descriptions. The graphical user interface includes a diagram display region to display one or more anatomical diagrams associated with a medical procedure. At least one diagram includes one or more user selectable regions corresponding to the user selectable medical codes.

Implementations can optionally include one or more of the following features. The one or more user selectable regions can provide a visual indication of a user selection of the corresponding medical code. The one or more user selectable regions can include one or more catheter insertion locations. The diagram display region can receive a user selection of one of the one or more catheter insertion locations and a user identification of at least one destination location. The selected catheter insertion location and the identified destination location represent two points on a catheter route. The diagram display region can receive a user selection of another destination location. The system can include a data storage device communicatively coupled to the one or more computer systems. The one or more computer systems can obtain medical codes stored in the data storage device based on the user selections of the insertion point and at least one of the two destinations.

Yet in another aspect, a system includes a data storage unit to store medical data associated with one or more catheter routes. The system also includes a route mapper communicatively coupled to the data storage unit. The route mapper performs the following: translate a description of one of the one or more catheter routes into standard medical codes, translate the description of one of the one or more catheter routes into a series of line segments.

Implementations can optionally include one or more of the following features. The data storage unit can store the medical data that includes a directed graph and a mapping table. The route mapper can traverse the directed graph based on the description to obtain the standardized medical codes. The description can include a sequence of anatomy identifiers. Also, the route mapper can identify from the mapping table the one or more line segments associated with each anatomy identifier. The system can include an interface handler in communication with the route mapper. The interface handler can provide a visual indication of the catheter route.

The subject matter described in this specification potentially can provide one or more advantages. For example, the techniques of visualizing the documentation and coding of medical procedures tends to be more efficient and faster than a manual process. In addition, the techniques of visualizing the documentation and coding of medical procedures generally do not require as high a level of expertise on the part of the medical coder to understand the nature of the interventional surgical procedures and nuances of the coding systems. Further, multiple display options can be provided to help compensate for variations in vascular anatomy among different people and to provide multiple entry and exit locations for the catheters used in some surgical procedures.

The subject matter described in this specification can be implemented as a method or as a system or using computer program products, tangibly embodied in information carriers, such as a CD-ROM, a DVD-ROM, a semiconductor memory, and a hard disk. Such computer program products may cause a data processing apparatus to conduct one or more operations described in this specification.

In addition, the subject matter described in this specification also can be implemented as a system including a processor and a memory coupled to the processor. The memory may encode one or more programs that cause the processor to perform one or more of the method acts described in this specification. Further, the subject matter described in this specification can be implemented using various data processing machines.

DESCRIPTION OF DRAWINGS

Like reference symbols in the various drawings indicate like elements.

DETAILED DESCRIPTION

Among other things, the following describes techniques, systems and computer program products for visualizing documentation and medical coding of a medical procedure. For illustrative purpose, the following is described with respect to medical procedures that can be performed with minimally invasive techniques using image-guided catheters that are inserted into blood vessels. For example, a catheter can be introduced into a blood vessel at one part of the body, such as the upper arm or groin area, and routed through the vessels to reach parts of the body that may be diseased or injured. Conditions such as blood clots, arteriosclerosis, aneurysms, and embolisms may be diagnosed and treated using such interventional procedures. However, other medical procedures that can be visualized are also equally compatible with the techniques described in this specification.

Figure 1A:
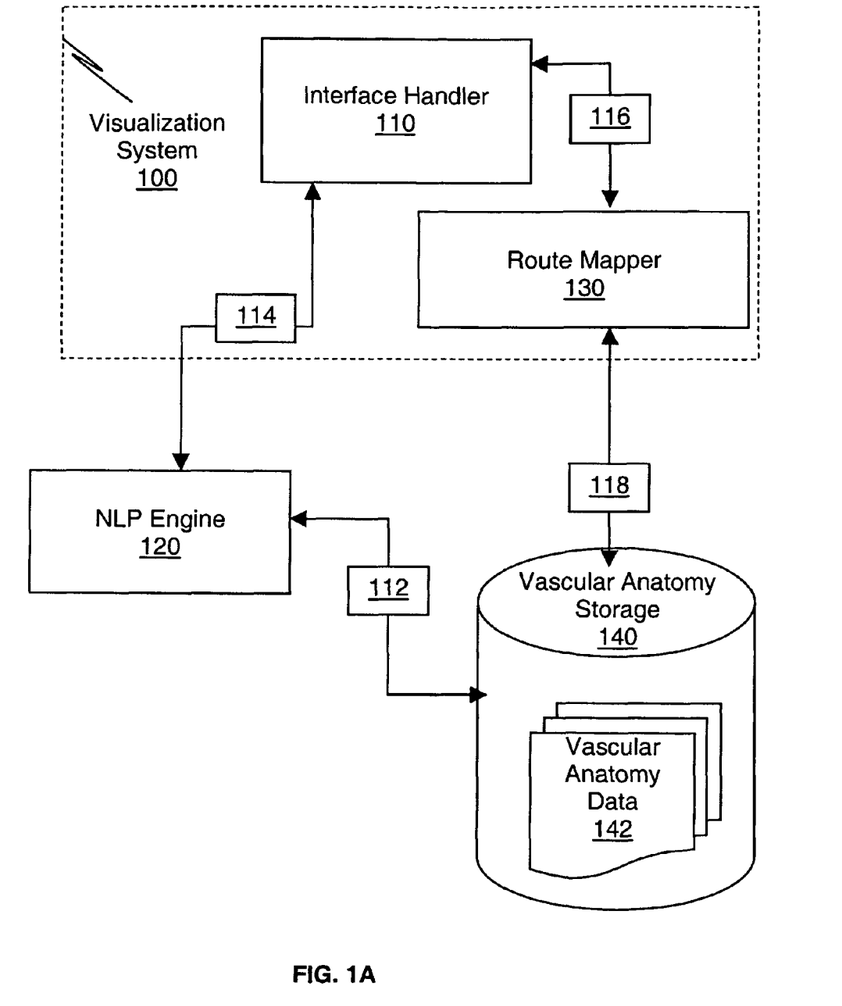
FIG. 1A is a functional block diagram of a visualization system.

FIG. 1 is a functional diagram illustrating a system 100 for providing a visual aid during physician documentation generation and/or medical coding of a medical procedure. The system 100 includes an interface handler 110 and a route mapper 130 that are coupled together over a bi-directional communication link 116. The interface handler 110 is also coupled to a natural language processing (NLP) engine 120 over a bi-directional communication link 114. The interface handler 110, the route mapper 130, and the NLP engine 120 can be implemented as one or more software application modules or one or more data processing devices executing one or more software application modules. In addition, the NLP engine 120 can be substantially as described in U.S. Pat. No. 6,915,254 entitled "Automatically Assigning Medical Codes Using Natural Language Processing", the entire contents of which are incorporated by reference.

Using a bi-directional communication link 118, the route mapper module 130 is coupled to a data storage device 140 that stores various vascular anatomy data 142. The NLP engine 120 is also coupled to the data storage device 140 over a bi-directional communication link 112. The data storage device 140 can include one or more network appliances, one or more local storage devices, etc. that maintains a database of vascular anatomy data. The bi-directional communication links 112, 114 and 116 include one or more wired or wireless communications links such as Universal Serial Bus, FireWire, WiFi, WiMax, Bluetooth, etc.

The NLP engine 120 assigns medical codes from a narrative text document (medical documentations or patient record) associated with a surgical procedure. The NLP engine 120 is designed to recognize, extract, and codify surgical procedures (e.g., catheterization procedures, including the specific catheter route) by accessing the database of vascular anatomy data 142. In addition, the NLP engine 120 is designed to generate a narrative text template of a surgical procedure (e.g., a catheter route and associated interventional procedures based on user-selected insertion and destination points.)

The route mapper 130 performs two primary functions. First, the route mapper 130 translates a description of a catheter route into a codified form. A codified form includes standard medical codes, such as CPT codes. Second, the route mapper translates a description of a catheter route into a series of line segments on the vascular anatomy diagrams. The description of a catheter route is defined by an ordered sequence of anatomy identifiers with each anatomy identifier representing one part of the anatomy, such as a blood vessel. For example, the string "Artery_Common_Femoral_Right, Artery_Internal_Iliac_Right, Aorta_Abdominal, Artery_Renal_Right" represents a description of a catheterization procedure that was inserted at the right common femoral artery, passed through the right internal iliac artery and abdominal aorta, and ended at the right renal artery. This description is generated by the NLP engine 120. The NLP engine 120 creates a description by scanning a free text description of a surgical note and, using techniques described in U.S. Pat. No. 6,915,254, contents of which are incorporated by reference, generates the anatomy identifiers that correspond to the parts of the anatomy related to the documented surgical procedure. Alternatively, a description can be produced by the interface handler 110 based upon the user selected anatomy regions using the vascular anatomy data 142 to translate each selected region to a corresponding anatomy identifier.

The vascular anatomy data 142 has two components, a directed graph and a mapping table. The directed graph has the following structure. Each vertex in the graph represents one part of the anatomy and an edge represents a direct physical connection between two parts of the anatomy. Each vertex corresponds to one anatomy identifier in a description. The graph is directed to denote the allowable directions in which to route a catheter. The edges of the graph are also annotated to identify branches in the vascular anatomy. For example, the right common femoral artery and right internal iliac artery are different parts of the same blood vessel. Thus, there is no branch in between the right common femoral artery and the right internal iliac artery. However, the abdominal aorta branches into the right and left internal iliac arteries. Therefore, the connecting edge between the abdominal aorta and right internal iliac artery is identified in the graph as a branch. The route mapper 130 traverses the directed graph and applies heuristics to determine the standardized codes, such as CPT codes, based upon the distance and branch count between the insertion and destination points as specified in published coding guidelines.

To translate a description of a catheter route into a series of line segments, the route mapper 130 uses the mapping table in the vascular anatomy data 142 to lookup the line segment(s) associated with each identifier. A data record in the mapping table has three parts: (1) anatomy identifier, (2) diagram identifier, and (3) line segments. The route mapper 130 fetches the record for each anatomy identifier in a description that corresponds to the diagram selected within the vascular anatomy diagram panel 106. The line segments are used by the interface handler 110 to provide a visual indication (e.g., highlight) of the catheter route on the vascular anatomy diagram panel 106. Alternatively, this table is used in reverse to generate a description by mapping from user selected line segments to a sequence of anatomy identifiers.

Figure 1B:
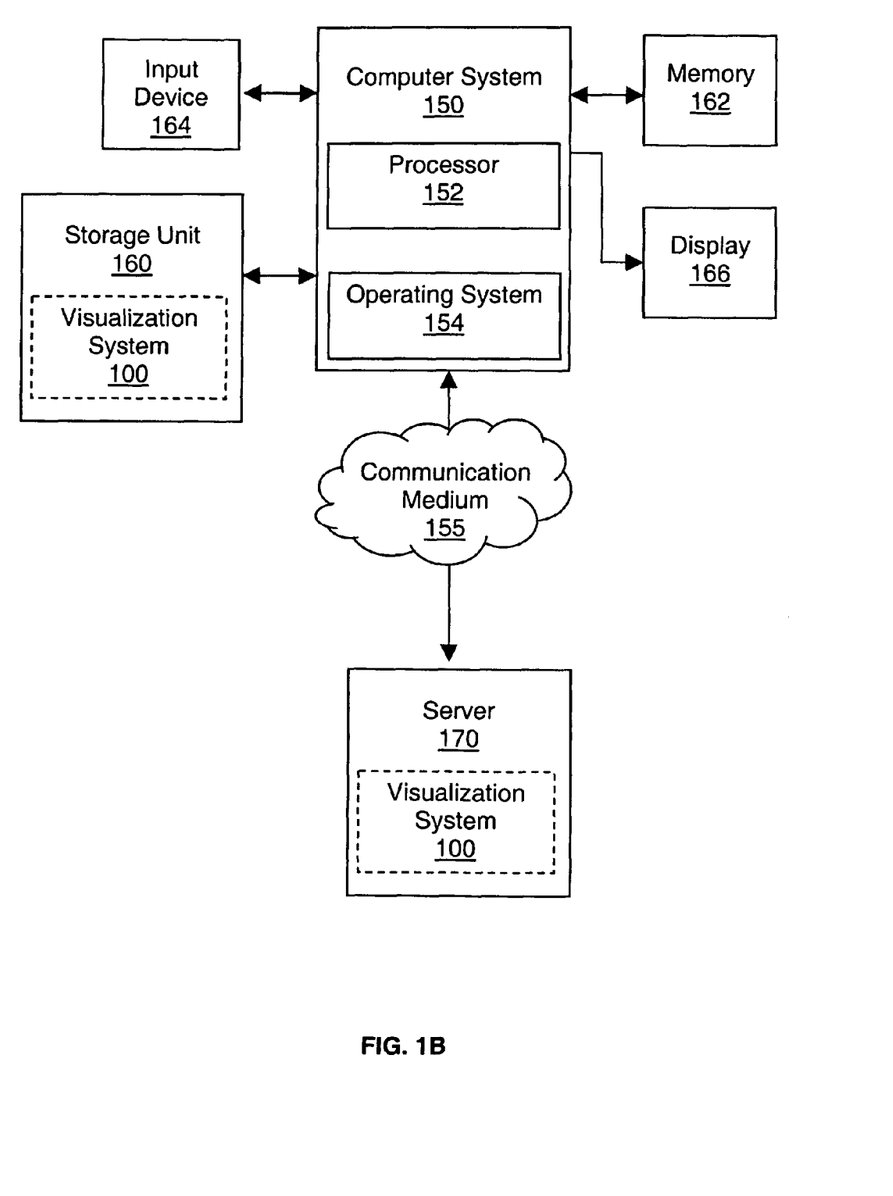
FIG. 1B is a functional block diagram of a visualization system executing on a computer system.

FIG. 1B is a block diagram illustrating the visual system 100 implemented as software or a set of machine executable instructions executing on a computer system 150 such as a local server in communication with other internal and/or external computers or servers 170 through a communication link 155, such as a local network or the internet. The communication link 155 can include a wired and/or a wireless network communication protocol. A wired network communication protocol can include local wide area network (WAN), broadband network connection such as Cable Modem, Digital Subscriber Line (DSL), and other suitable wired connections. A wireless network communication protocol can include WiFi, WIMAX, BlueTooth and other suitable wireless connections.

The computer system 150 includes a central processing unit (CPU) 152 executing a suitable operating system (OS) 154 (e.g., Windows® OS, Apple® OS, UNIX, LINUX, etc.), a storage device 160 and a memory device 162. The computer system can optionally include other peripheral devices, such as an input device 164 and a display device 166. The storage device 160 can include nonvolatile storage units such as a read only memory (ROM), a CD-ROM, a programmable ROM (PROM), erasable program ROM (EPROM) and a hard drive. The memory device 162 can include volatile memory units such as random access memory (RAM), dynamic random access memory (DRAM), synchronous DRAM (SDRAM) and double data rate-synchronous DRAM (DDRAM). An input device can include a keyboard, a mouse, a touch pad and other suitable user interface devices. A display device 166 can include a Cathode-Ray Tube (CRT) monitor, a liquid-crystal display (LCD) monitor, or other suitable display devices. Other suitable computer components such as input/output devices can be included in the computer system 150.

In some implementations, the visualization system 100 is implemented as a web application maintained on a network server such as a web server. In such implementations, a user accesses the visualization system 100 from a remote site using a client-side application such as a web browser. The visualization system 100 can be implemented as other suitable web/network-based applications using any suitable web/network-based computer programming languages. For example C/C++, an Active Server Page (ASP), and a JAVA Applet can be implemented. When implemented as a web application, multiple end users are able to simultaneously access and interface with the visualization system 100 without having to maintain individual copies on each end user computer. In some implementations, the visualization system 100 is implemented as a local application executing in a local end user computer or as client-server modules, either of which may be implemented in any suitable programming language, environment or as a hardware device with the application's logic embedded in the logic circuit design or stored in memory such as PROM, EPROM, Flash, etc.

Figure 2:
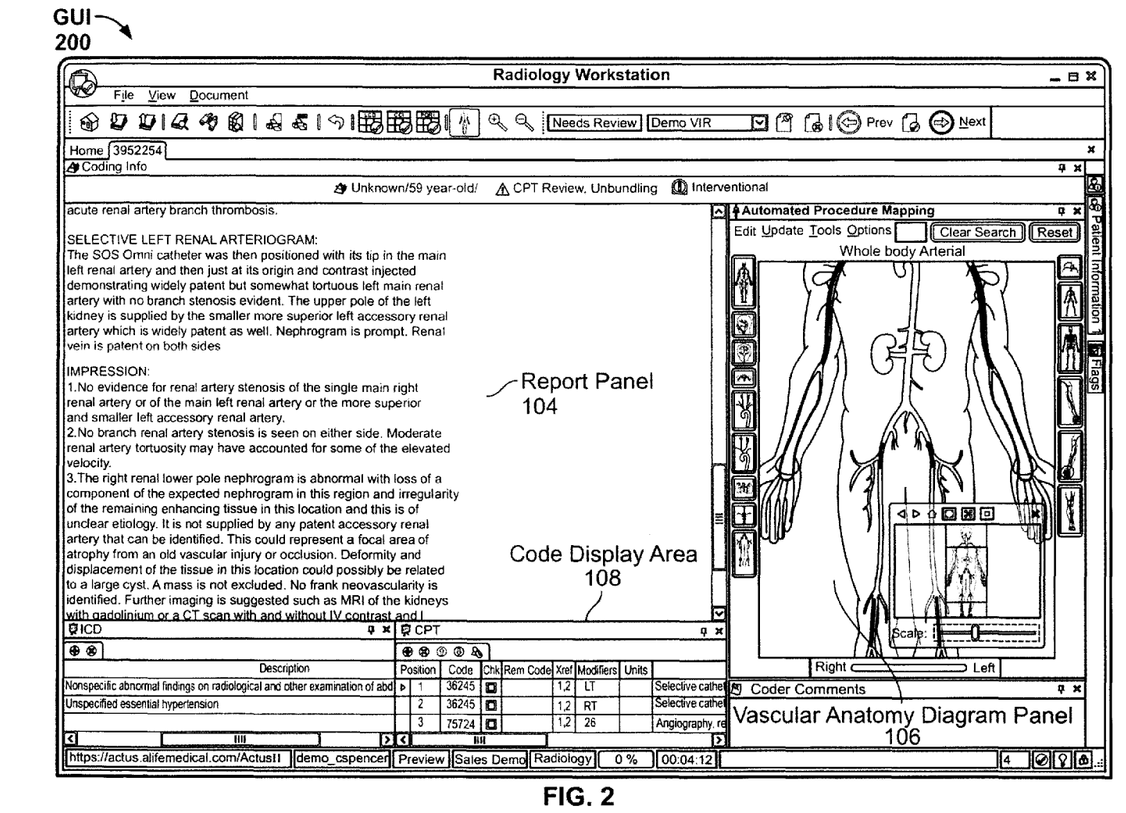
FIG. 2 shows an example visual layout of a Graphical User Interface.

FIG. 2 illustrates an exemplary visual layout of a graphical user interface (GUI) 200. The GUI 200 enables bi-directional communication between the user and the system with natural language processing functions to provide documentation and coding of medical procedures, such as interventional surgical procedures. The bi-directional graphical user interface allows a user to visualize the narrative text, vascular anatomy diagrams and medical codes.

The GUI 200 is 'bi-directional' in that the GUI 200 provides interactive functionality to display catheter routes from narrative text reports that have been processed by an NLP engine 120 and enter catheter routes for purposes of coding or documentation. The NLP Engine 120 assigns medical codes from narrative text using techniques similar to those described in U.S. Pat. No. 6,915,254. For example, the NLP Engine 120 is capable of recognizing, extracting, and codifying catheterization procedures, including the specific catheter route, using a database of vascular anatomy. In addition, the NLP Engine 120 is capable of generating a narrative text template of a catheter route and associated interventional procedures based on user-selected insertion and destination points on one or more anatomical diagrams.

Physician documentation of interventional surgical procedures can include a narrative text that describes all aspects of the procedure. This includes the reason for the procedure, identification and preparation of the insertion point, the anesthesia given to the patient, the specific instruments and surgical tools used, the route of the catheter through the body, the diagnostic tests or treatments performed at specific catheter placements, and the observed results of the tests or treatments.

Variations in anatomy among different people can be accounted for by providing various options and customization choices. For example, variations in anatomy may affect how vessels are interconnected, and various interconnections can be provided using various diagrams. Further, different choices can be provided to allow for various insertion and destination points for the catheters. With multiple destinations, route identification can be performed by incorporating the order of visit to the destination points and the paths between destination points.

The GUI 200 includes two user-interactive areas 104 and 106. The first user-interactive area 104, labeled in FIG. 2 as Report Panel, is designed to display narrative text describing a surgical procedure. For example, physician documentation and associated medical coding can be displayed in the Report Panel 104. The second user-interactive area 106, labeled in FIG. 2 as Vascular Anatomy Diagram Panel, is designed to display visual diagrams related to the narrative text in the first user-interactive area 104. For example, the vascular anatomy diagram panel 106 displays various anatomically correct diagrams for different body areas at varying levels of detail. The vascular anatomy diagram panel 106 can include various user-selectable GUI objects for providing additional user-interactive diagrams. For example, the vascular anatomy diagram panel 106 can be bordered by user-selectable thumbnail-sized icons that represent the available anatomy diagrams.

A user interaction (e.g., by clicking the mouse pointer on one of the thumbnail diagrams) with one of the thumbnail-sized icons opens the associated diagram in full-size view. Within the vascular anatomy diagram panel 106, the user may perform various user interactions including panning and zooming on the selected diagram and opening multiple diagrams. The vascular anatomy diagram panel 106 can further include additional user-interactive visual displays, such as detailed overlays (not shown) of blood vessel names and diagrams for both the arterial and venous systems and variant anatomy.

The GUI 200 enables various user interactive modes. In one mode, a medical coder can open up physician documentation or a patient record in the report panel 104 to perform coding of surgical procedures. Medical coding involves the assignment of codes from standardized code sets representing the clinically relevant aspects of clinician documentation or a patient medical record. Code sets, such as CPT® and ICD-9-CM, provide a system of numeric or alpha-numeric codes each with a standard definition and are used for both administrative and clinical purposes. The coding of interventional surgical procedures can be complex because the multiple aspects of an interventional surgical procedure that are captured and codified tend to require extensive knowledge of surgical practice, clinical terminology and coding rules and must be applied with high accuracy.

Coding an interventional surgical procedure includes providing a representation of the route of the catheter traveling through the blood vessels. For CPT coding, this can include the insertion point, the specific blood vessels the catheter passes through, the number and type of vessel branches, and the tests or treatments performed.

Additional user-interactive display region (e.g., a code display area 108) can be implemented to display the medical codes associated with the physician documentation or the patient record (i.e., narrative text). The code display area 108 is implemented to be displayed in one or more locations. For example, the code display area 108 can be displayed to overlay the report panel 104 or can be positioned directly below the report panel 104. Alternatively, the codes may be displayed as annotations on the anatomy diagrams.

Figure 3:
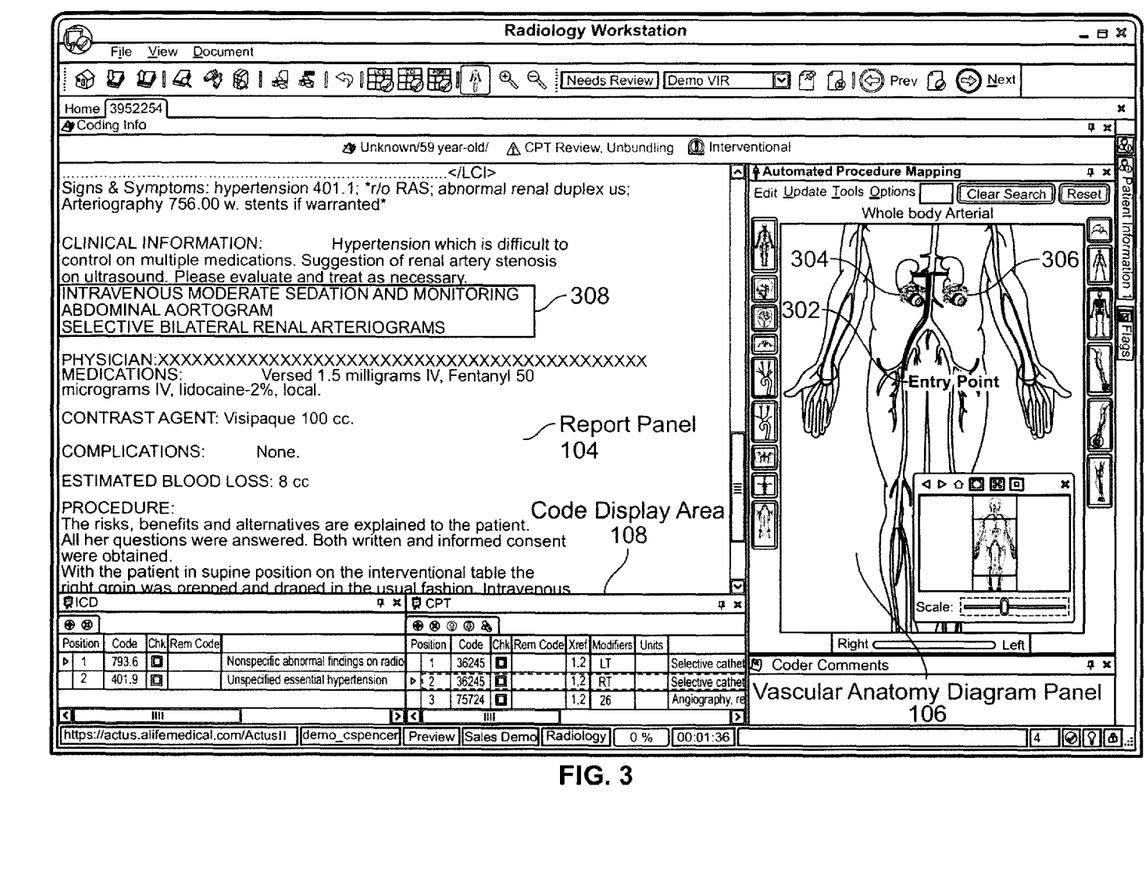
FIG. 3 shows another example visual layout of a Graphical User Interface that that links procedure documentation with medical codes and a vascular anatomy diagram.

FIG. 3 shows another example visual layout of a Graphical User Interface that links procedure documentation with medical codes and a vascular anatomy diagram. User selection of the codes displayed in the code grid area 108 activates the relevant portions of the body in one or more of the diagrams displayed in the vascular anatomy diagram panel 106. For example, in response to a detection of a user clicking on a code associated with a catheter-based procedure, the appropriate catheter route is activated (e.g., highlighted) on the selected vascular diagram(s) displayed in the vascular anatomy diagram panel 106. In addition, corresponding text within the report panel 104 is also highlighted 308. The selection of three CPT codes (36245, 36245, and 75724) in the code display area 108 highlights the relevant portions of the document in the report panel 104 and displays a route of a catheter through the arterial system on the vascular anatomy diagrams(s) in the vascular anatomy diagram panel 106. For example, CPT code 36245 can represent a first-order selective catheter placement for the arterial system in the abdominal, pelvic or lower extremity regions and is visualized by a red line 302 overlaying the arteries in the anatomy diagram. The CPT code 36245 can be repeated to represent both the catheterization of the right renal and left renal arteries. CPT code 75724 can represent the bilateral renal angiography and is visualized by the camera icons 304 and 306 on the anatomy diagram. The NLP engine 120 and route mapper 130 generates the information used to display the text highlights and catheter routes.

The code display area 108 can also enable the user to add a new procedure by selecting the catheter insertion and destination points on selected diagram(s) on the vascular anatomy diagram panel 106 and executing the route mapper 130. The route mapper 130 computes the path(s) based on the vascular anatomy data 140 associated with the selected insertion and destination points. In addition, the appropriate medical codes associated with the computed path(s) are returned and displayed in the code display area 108.

Figure 4:
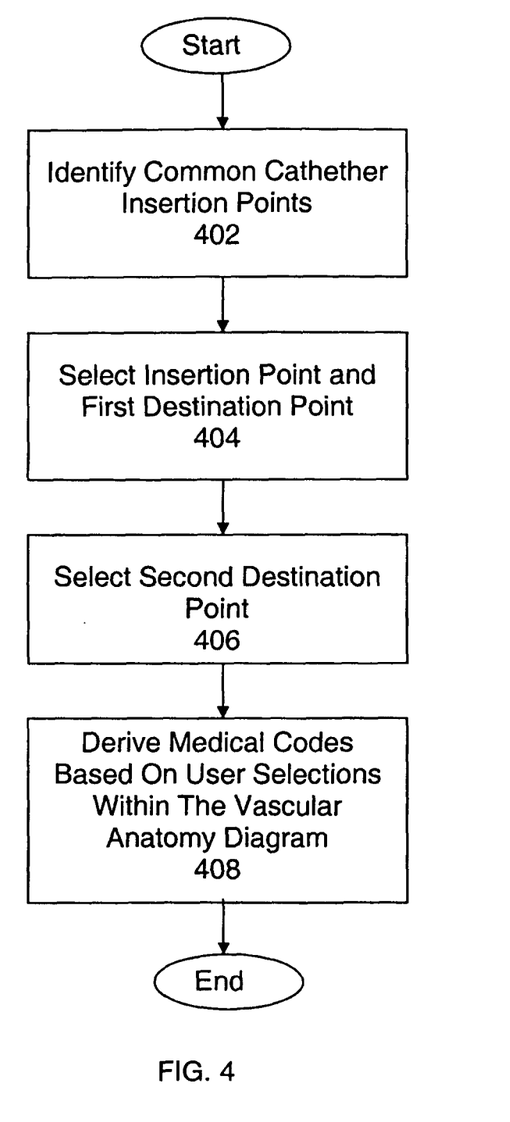
FIG. 4 shows an example process for adding a new procedure.

FIG. 4 shows an example process 400 for adding a new procedure. Common catheter insertion points are identified on an anatomical diagram (402). This enables a user to identify where to place the initial insertion point. For example, the location of the initial insertion point can be the right femoral artery (see FIG. 5A below.) The insertion point and first destination point is selected by the user and received by the system (404). For example, the user selection can be received using the GUI shown in FIG. 5B below. In the example shown in FIG. 5B, the use selected insertion point and first destination point is the right renal artery. A red line is used to visualize the route of the catheter from the right femoral artery to the right renal artery.

Figure 5A:
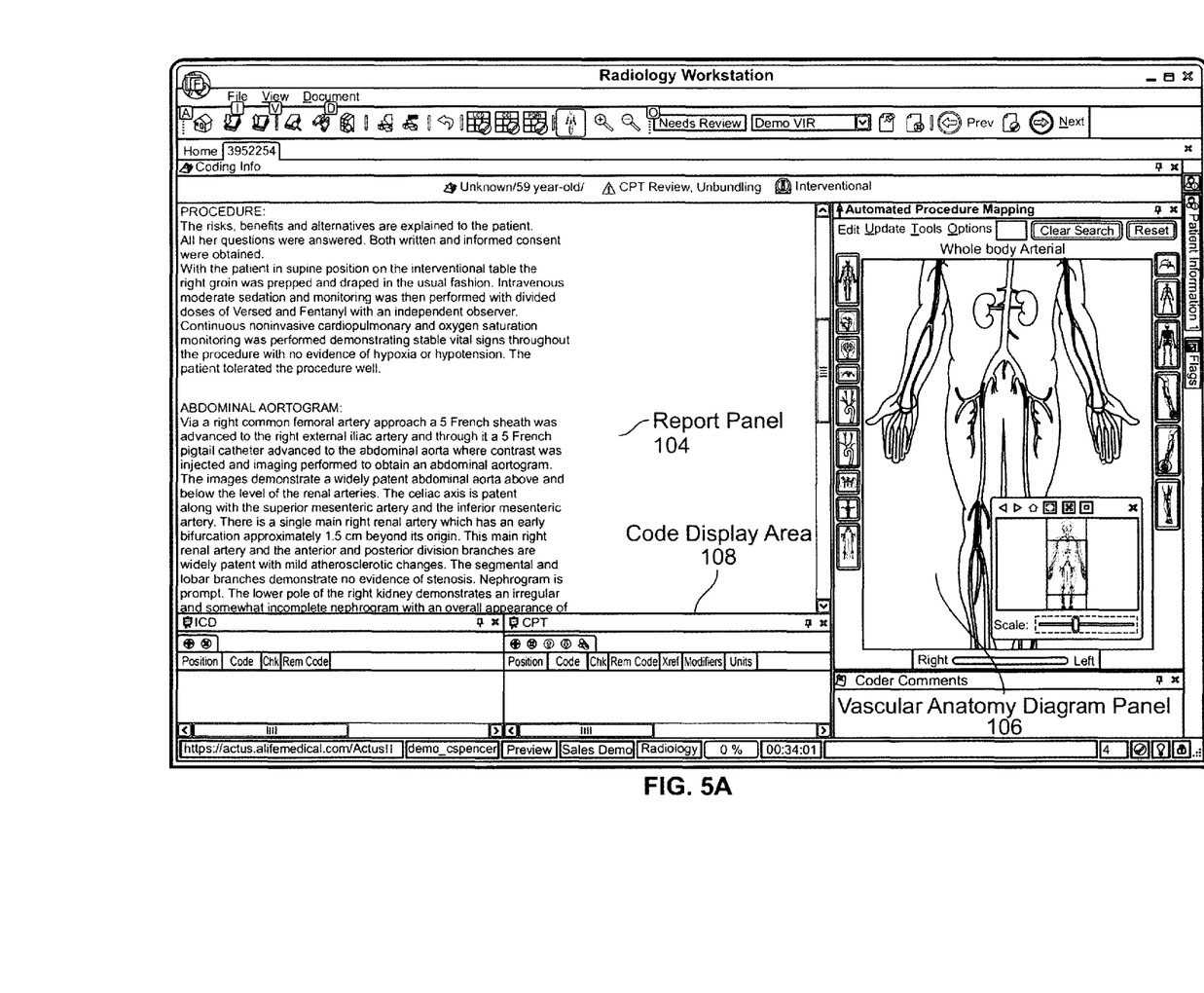
FIG. 5A shows an example Graphical User Interface that includes a visual representation of common catheter insertion points.
Figure 5B:
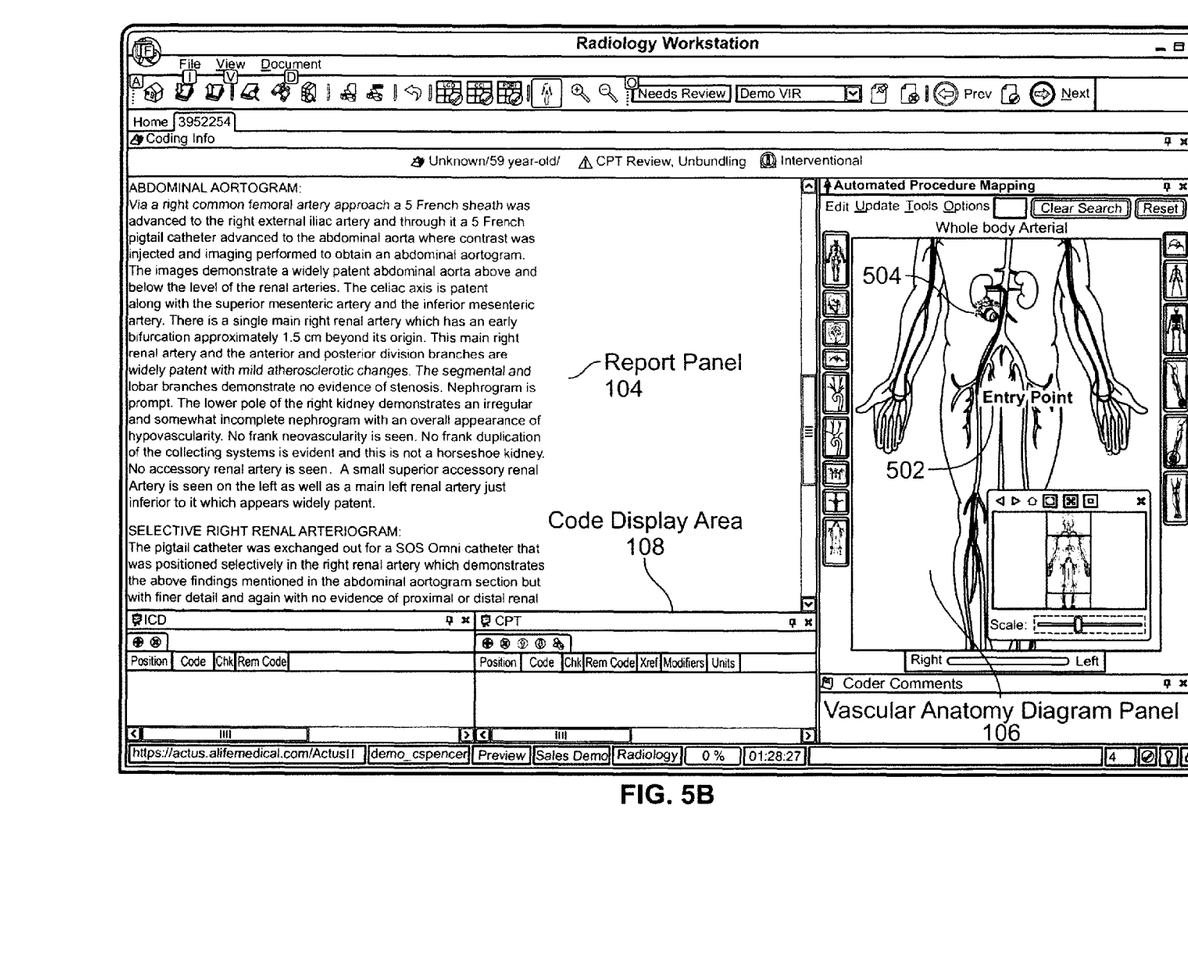
FIG. 5B shows an example Graphical User Interface that includes a visual representation of a catheter route to the right renal artery.
Figure 5C:
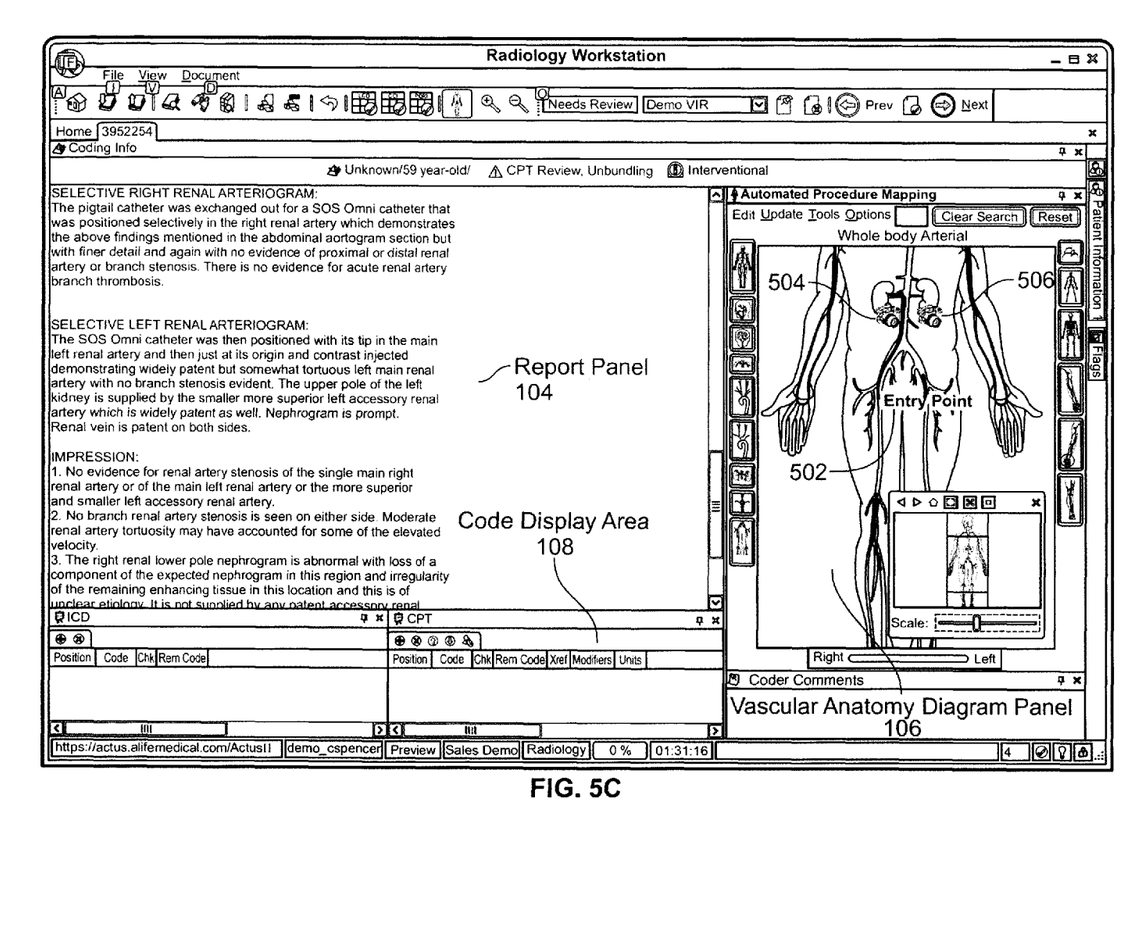
FIG. 5C shows an example Graphical User Interface that includes a visual representation of a catheter route to the left renal artery.

In addition, a user selection of a second destination point is received using the GUI shown in FIG. 5C, for example (406). In the example shown in FIG. 5C, the selected second destination point is at the left renal artery. Further, medical codes are derived based on the user selections within the vascular anatomy diagram (408). For example, the route mapper 130 can be executed through the vascular anatomy display area 108.

FIGS. 5A, 5B, 5C, and 5D show example GUIs used for adding a new procedure by user selection of insertion points on vascular anatomy diagrams. FIG. 5A shows a GUI that illustrates a visual representation of the common catheter insertion points as described with respect to FIG. 4 above. Using the GUI shown in FIG. 5A, a user can identify the common catheter insertion points. For the example procedure shown in FIG. 5A, the common insertion points include the right femoral artery.

FIG. 5B shows an example GUI used to enable a user selection of an insertion point and first destination point as described with respect to FIG. 4. In the example shown in FIG. 5B, a visual representation of a catheter route to the right renal artery is included. A darkened (e.g., red) line 502 is used to visualize the route of the catheter from the right femoral artery to the right renal artery. Also displayed is a camera icon 504 that represents an angiogram of the right renal artery.

FIG. 5C shows an example GUI used to enable a user selection of a second destination point as described with respect to FIG. 4 above. FIG. 5C includes a visual representation of a catheter route to the left renal artery. The red line 502 started in FIG. 5B is extended into the left renal artery in FIG. 5C. Also a second camera icon 506 represents an angiogram of the left renal artery.

Figure 5D:
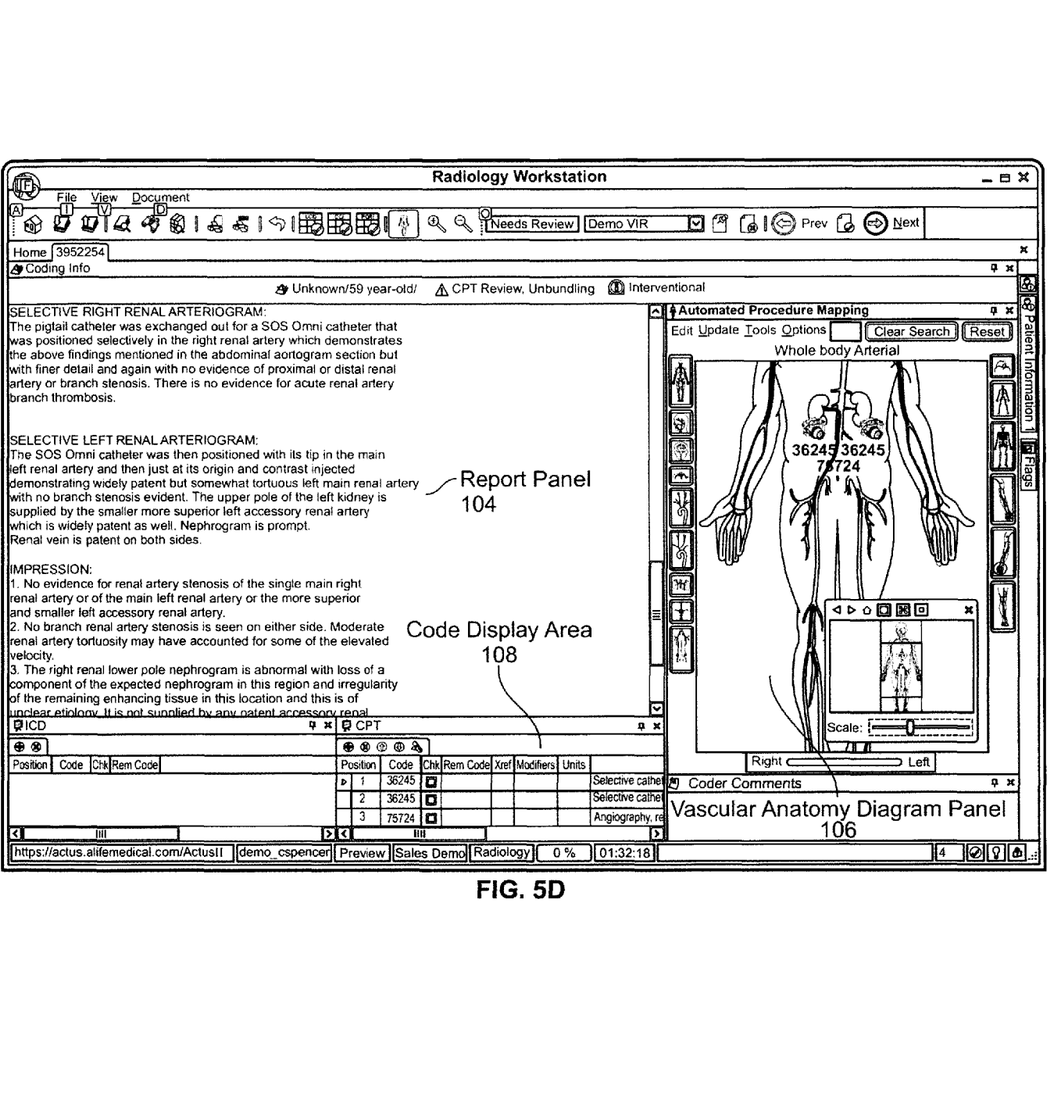
FIG. 5D shows an example Graphical User Interface that can be used to derive medical codes based upon user selections within a vascular anatomy diagram.

FIG. 5D shows an example GUI used to enable derivation of the medical codes based on the user selections within the vascular anatomy diagram. The route mapper 130 is executed through the vascular anatomy display area 108. In the example shown in FIG. 5D, three CPT codes (36245, 36245, and 75724) are returned from the route mapper 130 and annotated onto the anatomy diagram. The three CPT codes are also inserted into code display area 108. Similar to the example shown in FIG. 3, the procedure shown in FIG.

5D illustrates a first-order catheter placement into the right renal and left renal arteries with bilateral renal angiography.

In another mode, a physician can generate documentations for surgical procedures by entering narrative text using a keyboard, a mouse or other alternative input devices such as a microphone coupled with automatic speech recognition, electronic tablet with stylus, or a touch screen keyboard may be used. To generate text templates for the desired documentations, the physician selects one or more diagrams from the various available anatomy diagrams. From the selected one or more anatomy diagrams, the physician can select the desired anatomical locations that are relevant to a surgical procedure. For example, catheter insertion and destination points on the selected diagram(s) can be displayed in the vascular anatomy diagram panel 106. Based on the selected anatomical areas on the selected one or more diagrams, the NLP Engine 120 generates a free text description of the medical procedure with specific names for various anatomies such as blood vessel and vessel branches. The free text description is inserted directly into the narrative text displayed in the report panel 104. Once the textual description is generated, medical coding can be implemented as described with respect to the first mode.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "information carrier" comprises a "machine-readable medium" that includes any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal, as well as a propagated machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein does not require the particular order shown, or sequential order, to achieve desirable results. Also, the GUI described in this specification can be implemented using one or more computer systems that can present GUI to a user. The presented GUI includes commonly used GUI elements such as buttons, tabs, menu items, etc. than indicate to a user that user input is requested. Using these GUI elements, a user can provide the desired input to the system. Other embodiments may be within the scope of the following claims.

A number of implementations of the disclosure have been described. Nevertheless, it will be understood that various modifications may be made without departing from the scope of the disclosure including the claims.

What is claimed is:

1. A computer implemented method comprising:
   providing an anatomical diagram associated with a medical procedure, wherein the anatomical diagram includes a plurality of user selectable areas;
   receiving a user selection indicative of two or more user selectable areas of the plurality of user selectable areas on the anatomical diagram at a computer processor;
   if the two or more user selectable areas include a first user selectable area:
   using a natural language processing computer program to generate a first free text description of the received user selection;
   if the two or more user selectable areas do not include the first user selectable area:
   using the natural language processing computer program to generate a second free text description of the received user selection;
   using the first or second free text description to generate a procedural route for the medical procedure using the computer processor, the procedural route representing an anatomical path within a body of a patient; and
   displaying on an electronic display the procedural route representing the anatomical path within the body of the patient on the anatomical diagram.

2. The computer implemented method of claim 1, wherein the providing comprises: presenting the two or more user selectable areas to include one or more insertion locations.

3. The computer implemented method of claim 2, further comprising: receiving a user selection of one of the two or more insertion locations and a user identification of at least one destination location, wherein the selected insertion location and the identified destination location represent two points on the procedural route.

4. The computer implemented method of claim 3, further comprising: receiving a user selection of another destination location.

5. The computer implemented method of claim 4, further comprising: obtaining medical codes based on the user selections of the insertion point and at least one of the two destinations.

6. The computer implemented method of claim 5, wherein obtaining the medical codes comprises: translating the description of the medical procedure into medical codes, the medical codes including at least one of numeric codes and alpha-numeric codes descriptive of the medical procedure.

7. The computer implemented method of claim 1, wherein the computer processor is further configured to generate a visual indication on a portion of the first or second free text description corresponding to the received user selection.

8. The computer implemented method of claim 1, wherein using the first or second free text description to generate the procedural route further comprises generating a series of line segments corresponding to anatomy identifiers in the anatomical path, and wherein displaying on an electronic display the procedural route comprises displaying the series of line segments on corresponding anatomical portions of the anatomical diagram.

9. The computer implemented method of claim 1, wherein at least one of the first or second free text description comprises one or more of a reason for the medical procedure, an insertion point of the medical procedure, anesthesia used for the medical procedure, a medical instrument used in the medical procedure, a catheter placement for the medical procedure, a diagnostic test for the medical procedure, a diagnostic treatment for the medical procedure, or results associated with the medical procedure.

10. The computer implemented method of claim 1, wherein providing an anatomical diagram associated with a medical procedure includes selecting the anatomical diagram based on vascular anatomical variation.

* * * * *